United States Patent [19]

Seele et al.

[11] Patent Number: 5,039,815

[45] Date of Patent: Aug. 13, 1991

[54] 1-HALO-AZOLYLETHANE DERIVATIVES AND FUNGICIDES CONTAINING THEM

[75] Inventors: Rainer Seele, Fussgoenheim; Walter Himmele, Walldorf; Norbert Goetz, Worms; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 564,783

[22] Filed: Aug. 9, 1990

Related U.S. Application Data

[62] Division of Ser. No. 363,773, Jun. 9, 1989, abandoned.

[30] Foreign Application Priority Data

Jun. 11, 1988 [DE]  Fed. Rep. of Germany ....... 3819903

[51] Int. Cl.$^5$ ................... C07D 249/08; C07D 233/58
[52] U.S. Cl. .................................. 548/262.2; 548/341
[58] Field of Search .............................. 548/262.2, 341

[56] References Cited

U.S. PATENT DOCUMENTS 4,507,140  3/1985  Sugavanan ............................. 71/76
4,657,921  4/1987  Frick et al. ......................... 514/383

OTHER PUBLICATIONS

Bergamann et al., "W-Fluoracetophenone. III, etc", JACS, 79, p. 4178 (1957).
Neumuller, Rompps Chemie-Lexikon, Franckh'sche Verlagshandlung, Stuttgart, pp. 1336, 4245.

Primary Examiner—Mary C. Lee
Assistant Examiner—Patricia L. Morris
Attorney, Agent, or Firm—Oblon, Spivak, McClelland, Maier & Neustadt

[57] ABSTRACT

1-Halo-1-azolylethane derivatives of the formula I

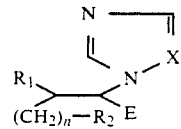

where $R^1$ and $R^2$ are $C_1$-$C_8$-alkyl, phenyl, biphenyl, naphthyl, benzyl, $C_3$-$C_8$-cycloalkyl or $C_3$-$C_8$-cycloalkenyl, each of which is unsubstituted or substituted,
  n is an integer from 1 to 5, or 0,
  E is Cl or Br, and
  X is CH or N,
their plant-tolerated acid addition salts and metal complexes, and fungicides containing these compounds.

5 Claims, No Drawings

1-HALO-AZOLYLETHANE DERIVATIVES AND FUNGICIDES CONTAINING THEM

This is a division of application Ser. No. 07/363,773, filed on June 9, 1989, now abandoned.

The present invention relates to new haloazole compounds, processes for their manufacture, and fungicides containing them.

The use of 1-(1,2,4-triazol-1-yl)-2-(2,4-dichlorophenyl)-pentane as a fungicide has been disclosed (Thomson, Agricultural Chemicals, Book IV, Fungicides, page 124, 1988).

We have now found that 1-halo-1-azolylethane derivatives of the general formula I

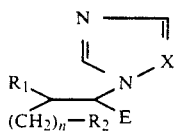

where $R^1$ and $R^2$ are $C_1$-$C_8$-alkenyl phenyl, biphenyl, naphthyl, benzyl, $C_3$-$C_9$-cycloalkyl or $C_3$-$C_8$-cycloalkenyl, each of which is unsubstituted or substituted by halogen, nitro, phenoxy, alkyl, alkoxy, amino or haloalkyl, each of 1 to 4 carbon atoms, n is an integer from 1 to 5, or 0, E is Cl or Br, and X is CH or N, and their plant-tolerated acid addition salts and metal complexes, have a better fungicidal action, especially on cereal diseases, than the prior art azole compounds.

The compounds of the formula I contain asymmetric carbon atoms amd may therefore occur as enantiomers and diastereomers. The invention encompasses both the pure isomers and mixtures of them. The diastereomer mixtures may be separated into their components by conventional methods, for example by fractional crystallization or by chromatography on silica gel. The racemates may be separated by conventional methods, for instance by formation of a salt with an optically active acid, separation of the diastereomeric salts and liberation of the enantiomers with the aid of a base.

Both the individual enantiomers and diastereomers, and mixtures thereof may be used as fungicidal active ingredients. $R^1$ and $R^2$ are identical or different and denote for example: methyl, ethyl, isopropyl, n-propyl, n-butyl, sec-butyl, tert.-butyl, n-pentyl, neopentyl, hexyl, octyl, trifluoromethyl, trichloromethyl, phenyl, 2-chlorophenyl, 2-fluorophenyl, 2-bromophenyl, 3-chlorophenyl, 3-bromophenyl, 3-fluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, 2-methoxyphenyl, 3-methoxyphenyl, 4-methoxyphenyl, 2,4-dimethoxyphenyl, 4-ethylphenyl, 4-isopropylphenyl, 4-tert.-butylphenyl, 4-tert.-butyloxyphenyl, 2-chloro-4-fluorophenyl, 2chlor-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, cyclopropyl, cyclobutyl, cyclopentyl, cyclohexyl, cyclooctyl, $C_6$-cycloalkenyl, 2-cyclohexenyl, 3-cyclohexenyl and norbornyl. n denotes 0, 1, 2, 3, 4 or 5. Examples of acid addition salts are the hydrochlorides, bromides, sulfates, nitrates, phosphates, oxalates and dodecylbenzenesulfonates. As the action of the salts is attributable to the cation, the anion is as a rule unimportant. The active ingredient salts according to the invention are produced by reacting the 1-halo-1-azolylethane derivatives I with the acids. Metal salts of active ingredients I, or of their salts, may be formed with copper, zinc, tin, manganese, iron, cobalt or nickel by reacting the 1-halo-1-azolylethane derivatives with appropriate metal salts, e.g., copper sulfate, zinc chloride and tin chloride. The compounds of the formula I may be prepared for instance by reacting a compound of the formula II

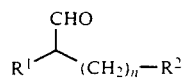

where $R^1$, $R_2$ and n have the above meanings, with a compound of the formula III

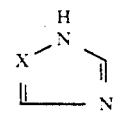

where X has the above meanings, in the presence of corresponding thionyl halides. The reaction is carried out at from $-30°$ to $80°$ C. in the presence or absence of a solvent or diluent. Preferred solvents and diluents are nitriles such as acetonitrile and propionitrile, ethers such as tetrahydrofuran, diethyl ether, dimethoxyethane, dioxane and diisopropyl ether, and in particular hydrocarbons and chlorohydrocarbons such as pentane, hexane, toluene, methylene chloride, chloroform, carbon tetrachloride and dichloroethane and appropriate mixtures thereof. The compounds of the formula II may be prepared in accordance with generally known aldehyde synthesis methods (Houben-Weyl-Müller, Methoden der organischen Chemie, Georg-Thieme-verlag, Stuttgart 1983, Vol. E 3. The following example illustrates the manufacture of the active ingredients.

Example 1

At 0° C., 13.1 g of thionyl chloride is added to a solution of 15.222 g of 1,2,4-triazole in 150 ml of methylene choride. After all has been added, the mixture is stirred for 30 minutes at room temperature (20° C.): subsequently, 15.5 g of 2,3-biphenylpropanal is added. After the mixture has been stirred at room temperature for 12 to 15 hours, 100 ml of water is added and the organic phase separated off. The aqueous phase which remains is extracted by shaking twice with methylene chloride, and the collected organic phases are washed twice with saturated sodium bicarbonate solution. The isolated organic phase !s then dried over sodium sulfate and concentrated. There is obtained 30.0 g (92%) of 1-chloro-1-(1,2,4-triazol-1-yl-)2,3-diphenylpropane.

The compounds listed in the table below may be obtained analogously to Example 1:

TABLE structure: pyrazole/triazole ring with N—X, attached to N with substituents R₁, R₂, E, (CH₂)ₙ

| Ex. | R¹ | R² | n | E | X | D1:D2* | IR (cm⁻¹) |
|---|---|---|---|---|---|---|---|
| 1 | C₆H₅ | C₆H₅ | 1 | Cl | N | 4:1 | 1506,1497,1275,1135,762,699 |
| 2 | C₆H₅ | 4-F—C₆H₄ | 1 | Cl | N | — | — |
| 3 | C₆H₅ | 2-F—C₆H₄ | 1 | Cl | N | — | — |
| 4 | C₆H₅ | 2-Cl—C₆H₄ | 1 | Cl | N | — | — |
| 5 | C₆H₅ | 4-Cl—C₆H₄ | 1 | Cl | N | — | — |
| 6 | C₆H₅ | 2,4-Cl₂—C₆H₃ | 1 | Cl | N | — | — |
| 7 | C₆H₅ | 2,4-Cl₂—C₆H₃ | 1 | Cl | CH | — | — |
| 8 | C₆H₅ | C₁₀H₇ | 1 | Cl | N | — | — |
| 9 | C₆H₅ | CH₃ | 1 | Cl | N | — | — |
| 10 | C₆H₅ | C₄H₉ | 1 | Cl | N | — | — |
| 11 | C₆H₅ | cyclohexyl | 1 | Cl | N | — | — |
| 12 | C₆H₅ | C₆H₅ | 0 | Cl | N | 1:1 | 1506,1499,1275,1134,742,703 |
| 13 | C₆H₅ | 4-F—C₆H₅ | 0 | Cl | N | — | — |
| 14 | C₆H₅ | 2-Cl—C₆H₅ | 0 | Cl | N | — | — |
| 15 | C₆H₅ | C₁₂H₉ | 0 | Cl | N | — | — |
| 16 | C₆H₅ | cyclohexyl | 0 | Cl | N | 1:1 | 2927,2854,1505,1450,1275,1135,703 |
| 17 | C₆H₅ | 3-cyclohexenyl | 0 | Cl | N | — | — |
| 18 | C₆H₅ | C₆H₅ | 2 | Cl | N | 3:1 | 1506,1496,1276,1135,750,700 |
| 19 | C₆H₅ | 4-F—C₆H₅ | 2 | Cl | N | — | — |
| 20 | C₆H₅ | 2-Cl—C₆H₅ | 2 | Cl | N | — | — |
| 21 | C₆H₅ | C₆H₅ | 3 | Cl | N | — | — |
| 22 | C₆H₅ | 4-Cl—C₆H₄ | 3 | Cl | N | — | — |
| 23 | 4-F—C₆H₄ | C₆H₅ | 0 | Cl | N | — | — |
| 24 | 4-F—C₆H₄ | 4-F—C₆H₄ | 0 | Cl | N | — | 1508,1229,1160,837 |
| 25 | 4-F—C₆H₄ | 2-F—C₆H₄ | 0 | Cl | N | 1:1 | 1510,1493,1276,1233,809,756 |
| 26 | 4-F—C₆H₄ | 2-Cl—C₆H₄ | 0 | Cl | N | — | — |
| 27 | 4-F—C₆H₄ | 4-Cl—C₆H₄ | 0 | Cl | N | — | — |
| 28 | 4-F—C₆H₄ | 2,4-Cl₂—C₆H₃ | 0 | Cl | N | — | — |
| 29 | 4-F—C₆H₄ | 4-OCH₃—C₆H₄ | 0 | Cl | N | — | — |
| 30 | 4-F—C₆H₄ | iso-C₃H₇ | 0 | Cl | N | 7:3 | 2959,1510,1275,1229,1136,841 |
| 31 | 4-F—C₆H₄ | 2-F—C₆H₄ | 1 | Cl | N | — | — |
| 32 | 4-F—C₆H₄ | 4-F—C₆H₄ | 2 | Cl | N | — | — |
| 33 | 2-Cl—C₆H₄ | 4-F—C₆H₄ | 0 | Cl | N | — | — |
| 34 | 2-Cl—C₆H₄ | 4-Cl—C₆H₄ | 0 | Cl | N | — | — |
| 35 | 2-Cl—C₆H₄ | 2,4-Cl₂—C₆H₃ | 1 | Cl | N | — | — |
| 36 | 2-Cl—C₆H₄ | CH₃ | 1 | Cl | N | — | — |
| 37 | 2-Cl—C₆H₄ | CH₃ | 2 | Cl | N | 1:1 | 2960,1506,1275,1135,753 |
| 38 | 4-Cl—C₆H₄ | 4-Cl—C₆H₄ | 0 | Cl | N | — | — |
| 39 | 4-Cl—C₆H₄ | 4-F—C₆H₄ | 1 | Cl | N | — | — |
| 40 | 4-Cl—C₆H₄ | CH₃ | 1 | Cl | N | — | — |
| 41 | 4-Cl—C₆H₄ | CH₃ | 2 | Cl | N | 2:1 | resin |
| 42 | 2,4-Cl₂—C₆H₃ | 4-F—C₆H₄ | 0 | Cl | N | — | — |
| 43 | 2,4-Cl₂—C₆H₃ | 2-Cl—C₆H₄ | 0 | Cl | N | — | — |
| 44 | 2,4-Cl₂—C₆H₃ | CH₃ | 1 | Cl | N | 1.2:1 | 2970,1506,1476,1275,1199,1135,805 |
| 45 | 2,4-Cl₂—C₆H₃ | CH₃ | 2 | Cl | N | 1:1 | 2961,1506,1475,1275,1199,1135,797 |
| 46 | 2,4-Cl₂—C₆H₃ | CH₃ | 3 | Cl | N | 9:1 | 2958,1506,1475,1275,1135,804 |
| 47 | cyclohexyl | 4-F—C₆H₄ | 1 | Cl | N | — | — |
| 48 | cyclohexyl | 2-Cl—C₆H₄ | 1 | Cl | N | — | — |
| 49 | cyclohexyl | 2,4-Cl₂—C₆H₃ | 1 | Cl | N | — | — |
| 50 | cyclohexyl | 2-Cl—C₆H₄ | 2 | Cl | N | — | — |
| 51 | CH₃ | 4-F—C₆H₄ | 0 | Cl | N | — | — |
| 52 | CH₃ | 2-Cl—C₆H₄ | 0 | Cl | N | — | — |
| 53 | CH₃ | 4-Cl—C₆H₄ | 1 | Cl | N | 1:1 | 1506,1492,1275,1136,1015,811 |
| 54 | CH₃ | 4-F—C₆H₄ | 1 | Cl | N | 2:1 | 1511,1276,1223,1136,838 |
| 55 | CH₃ | 4-isopropyl-C₆H₄ | 1 | Cl | N | 1:1 | 2961,2934,1508,1276,1136,1004,818 |
| 56 | CH₃ | 4-tert-butyl-C₆H₄ | 1 | Cl | N | — | — |
| 57 | CH₃ | 4-OCH₃-C₆H₄ | 1 | Cl | N | 2:1 | 1514,1275,1255,1033,833,768 |

TABLE-continued

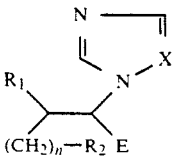

| Ex. | R¹ | R² | n | E | X | D1:D2* | IR (cm⁻¹)/m.p. |
|---|---|---|---|---|---|---|---|
| 58 | $CH_3$ | -C₆H₄-OC₂H₅ (para) | 1 | Cl | N | 1:1 | 2979,1611,1511,1275,1248,1047 |
| 59 | $CH_3$ | -C₆H₄-OC₃H₇ (para) | 1 | Cl | N | 1:1 | 2966,1611,1511,1275,1250,1135 |
| 60 | $CH_3$ | 4-$NO_2$—$C_6H_4$ | 2 | Cl | N | — | — |
| 61 | $CH_3$ | 2-F—$C_6H_4$ | 3 | Cl | N | — | — |
| 62 | $CH_3$ | $CH(C_6H_5)_2$ | 0 | Cl | N | 1:1 | 1496,1451,1277,1137,748,705 |
| 63 | tert.-butyl | 4-Cl—$C_6H_4$ | 0 | Cl | N | — | — |
| 64 | tert.-butyl | 4-F—$C_6H_4$ | 0 | Cl | N | — | — |
| 65 | tert.-butyl | 2-Cl—$C_6H_4$ | 0 | Cl | N | — | — |
| 66 | tert.-butyl | 2,4-$Cl_2$—$C_6H_3$ | 0 | Cl | N | — | — |
| 67 | tert.-butyl | 4-Cl—$C_6H_4$ | 1 | Cl | N | — | — |
| 68 | tert.-butyl | 4-F—$C_6H_4$ | 1 | Cl | N | — | — |
| 69 | tert.-butyl | 4-Cl—$C_6H_4$ | 2 | Cl | N | — | — |
| 70 | tert.-butyl | 4-Cl—$C_6H_4$ | 3 | Cl | N | — | — |
| 71 | tert.-butyl | cyclohexyl | 0 | Cl | N | — | — |
| 72 | tert.-butyl | cyclohexyl | 1 | Cl | N | — | — |
| 73 | tert.-butyl | cyclohexyl | 1 | Cl | N | — | — |
| 74 | 2,4-$Cl_2$—$C_6H_3$ | $CH_3$ | 1 | Cl | CH | 1:1 | 82–88° |
| 75 | 2,4-$Cl_2$—$C_6H_3$ | $CH_3$ | 2 | Cl | CH | 1:1 | 78–82° |
| 76 | $C_6H_5$ | $C_6H_5$ | 0 | Br | N | — | — |
| 77 | $C_6H_5$ | $C_6H_5$ | 1 | Br | N | 1:1 | 1506,1497,1454,1274,1133,700 |
| 78 | $C_6H_5$ | $C_6H_5$ | 2 | Br | N | — | — |
| 79 | $C_6H_5$ | cyclohexyl | 0 | Br | N | — | — |
| 80 | 4-F—$C_6H_4$ | iso-$C_3H_7$ | 0 | Br | N | — | — |
| 81 | 2,4-$Cl_2$—$C_6H_3$ | $CH_3$ | 1 | Br | N | — | — |
| 82 | 2,4-$Cl_2$—$C_6H_3$ | $CH_3$ | 2 | Br | N | 1:1 | 2961,2935,1506,1475,1274,1133,823 |
| 83 | $CH_3$ | 4-F—$C_6H_4$ | 0 | Br | N | — | — |
| 84 | $CH_3$ | -C₆H₄-iso-C₃H₇ (para) | 1 | Br | N | 1:1 | 2963,2933,2507,1421,1274,1134,817 |
| 85 | $CH_3$ | -C₆H₄-OC₂H₅ (para) | 1 | Br | N | 1:1 | 2979,1611,1511,1249,1047 |
| 86 | $CH_3$ | -C₆H₄-OC₃H₇ (para) | 1 | Br | N | 1:1 | 2965,1611,1511,1250,1134 |
| 87 | $CH_3$ | —$CH(C_6H_5)_2$ | 0 | Br | N | — | — |
| 88 | —$C(CH_3)_3$ | 4-Cl—$C_6H_4$ | 0 | Br | N | — | — |
| 89 | $C_6H_5$ | $CH_3$ | 0 | Cl | N | 3:1 | resin |
| 90 | $C_6H_5$ | $CH_3$ | 2 | Cl | N | 3:1 | 2960,1506,1275,1135,700 |
| 91 | $C_6H_5$ | $CH_3$ | 2 | Cl | CH | 1,2:1 | 2959,1229,1153,1088,754 |
| 92 | 4-F—$C_6H_4$ | $CH_3$ | 3 | Cl | N | 2:1 | 2958,1510,1276,1226,840 |
| 93 | 4-Cl—$C_6H_4$ | $C_2H_5$ | 5 | Cl | N | 2:1 | 2927,1505,1492,1275,1135,1015 |
| 94 | 4-F—$C_6H_4$ | 2-F—$C_6H_4$ | 0 | Cl | CH | 1:1 | 1511,1491,1230,1078,807,756 |
| 95 | 4-Cl—$C_6H_4$ | $CH_3$ | 0 | Cl | N | 3:1 | 1506,1495,1275,1135,1015,836,777 |
| 96 | 4-Cl—$C_6H_4$ | $CH_3$ | 2 | Cl | CH | 2:1 | 2960,1492,1092,1015,778 |
| 97 | 4-Cl—$C_6H_4$ | $CH_3$ | 5 | Cl | N | 2:1 | 2929,1506,1492,1275,1135,1015,765 |
| 98 | 2,4-$Cl_2$—$C_6H_3$ | $CH_3$ | 2 | Cl | N | 2:1 | 2958,1506,1475,1275,1135,804 |
| 99 | 2,4-$Cl_2$—$C_6H_3$ | $CH_3$ | 2 | Cl | CH | 3:7 | 2957,1489,1478,1226,1076,802 |
| 100 | 2-Cl—$C_6H_4$ | $CH_3$ | 5 | Cl | CH | 2:1 | resin |
| 101 | 3-Cl—$C_6H_4$ | $CH_3$ | 2 | Cl | N | 1:1 | 2961,1506,1275,1135,1001,767 |
| 102 | 3,4-$Cl_2$—$C_6H_3$ | $CH_3$ | 1 | Cl | N | 1:1 | 1506,1472,1275,1134,778,776 |
| 103 | 4-Cl—$C_6H_4$ | 2-Cl—$C_6H_4$ | 0 | Cl | N | 1:1 | 1506,1493,1275,1133,1015,754 |

TABLE-continued

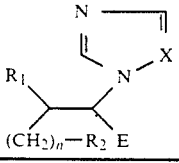

| Ex. | R¹ | R² | n | E | X | D1:D2* | IR (cm⁻¹) |
|---|---|---|---|---|---|---|---|
| 104 | 4-Cl—$C_6H_4$ | 2-Cl—$C_6H_4$ | 0 | Cl | CH | 1:1 | 1492,1227,1091,1015,754,736 |
| 105 | 2,4-$Cl_2$—$C_6H_3$ | $CH_3$ | 5 | Cl | N | 1:1 | 1506,1475,1275,1135,801,791 |
| 106 | 2,4-$Cl_2$—$C_6H_3$ | $C_3H_7$ | 5 | Cl | N | 1:1 | 2926,1505,1475,1275,1134,825 |
| 107 | 2-Cl—$C_6H_4$ | $C_2H_5$ | 5 | Cl | N | 1:1 | 2927,1505,1275,1135,752 |
| 108 | 4-$C_6H_5O$—$C_6H_4$ | $CH_3$ | 5 | Cl | N | 7:2 | 2929,1506,1489,1241,872 |
| 109 | 4-$C_6H_5O$—$C_6H_4$ | $CH_3$ | 1 | Cl | N | 2:1 | 1589,1506,1489,1239,872 |

| Ex. | R¹ | R² | n | E | X | D1:D2* | IR (cm⁻¹) |
|---|---|---|---|---|---|---|---|
| 110 | 2-naphthyl | $CH_3$ | 1 | Cl | N | 1.2:1 | 1506,1275,1135,780 |
| 111 | 2-naphthyl | $CH_3$ | 3 | Cl | N | 1:1 | 2957,1506,1275,1135,778 |
| 112 | 2-naphthyl | $CH_3$ | 5 | Cl | N | 1:1 | 2928,1506,1275,1135,777 |
| 113 | p-$C_6H_5$—$C_6H_4$ | $CH_3$ | 1 | Cl | N | — | — |
| 114 | 4-F—$C_6H_4$ | $C_3H_7$ | 5 | Cl | N | 1:1 | 2927,1510,1276,1226,1135,840 |
| 115 | 2,4-$Cl_2$—$C_6H_3$ | $CH_3$ | 3 | Cl | CH | 2:1 | resin |
| 116 | $CH_3$ | 4-$OCH_3$—$C_6H_4$ | 1 | Cl | N | 3:1 | 1512,1250,1035,819 |
| 117 | 4-F—$C_6H_4$ | 2-Cl—$C_6H_4$ | 0 | Cl | N | 1:1 | 1509,1276,1233,1059,808,750 |
| 118 | 4-F—$C_6H_4$ | 2-Cl—$C_6H_4$ | 0 | Cl | CH | 1:1 | resin |
| 119 | 4-F—$C_6H_4$ | $C_6H_4$ | 0 | Cl | N | 1:1 | 1510,1276,1227,1135,809,732 |
| 120 | 4-F—$C_6H_4$ | $C_6H_4$ | 0 | Cl | CH | 1:1 | 1602,1510,1496,1228,813,730 |
| 121 | 4-F—$C_6H_4$ | 4-Cl—$C_6H_4$ | 0 | Cl | N | — | 112° C. |

*Ratio of the diastereomers obtained

In general terms the novel compounds are extremely effective on a broad spectrum of phytopathogenic fungi, in particular those from the Ascomycetes and Basidiomycetes classes. Some of them have a systemic action and can be used as foliar and soil fungicides. The fungicidal compounds are of Particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits. The novel compounds are particularly useful for controlling the following plant diseases:

Erysiphe graminis in cereals,
Erysiphe cichoracearum and Sphaerotheca fuliginea in cucurbits,
Podosphaera leucotricha in apples,
Uncinula necator in vines,
Puccinia species in cereals,
Rhizoctonia species in cotton and lawns,
Ustilago species in cereals and sugar cane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and verticillium species in various plants,
Plasmopara viticola in qrapes,
Alternaria species in fruit and vegetables.

The compounds are applied by spraying or dusting the plants with the active ingredients, or treating the seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, of example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, chlorinated aromatics (e.g., chlorobenzenes), paraffins (e.g., crude oil fractions), alcohols (e.g., methanol, butanol), ketones (e.g., cyclohexanone, amines (e.g., ethanolamine, dimethylformamide, and water; carriers such as ground natural minerals (e.g., kaolins, aluminas, talc and chalk) and ground synthetic minerals (e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose. The fungicidal agents generally contain from 0.1 to 95, and preferably from 0.5 to 90 wt% of active ingredient. The application rates are from 0.2 to 3 kg or more of active ingredient per hectare, depending on the type of effect desired. The novel compounds may also be used for protecting materials, for example against Paecilomyces variotii. The agents and the ready-to-use formulations prepared from them, such as solutions, emulsions, suspensions, powders, dusts, pastes and granules, are applied in conventional manner, for example by spraying, atomizing, dusting, scattering, dressing or watering. Examples of formulations are given below. I. 90 parts by weight of compound no. 74 is mixed with 10 parts by weight of N-methyl-α-pyrrolidone. A mixture is obtained which is suitable for application in the form of very fine drops. II. 20 parts by weight of compound no. 89 is dissolved in a mixture consisting of 80 parts by weight of xylene, 10 parts by weight of the adduct of 8 to 10 moles of ethylene oxide and 1 mole of oleic acid-Nmonoethanolamide, 5 parts by weight of the calcium salt of dodecylbenzenesulfonic acid, and 5 Parts by weight of the adduct of 40 moles of ethylene oxide and 1 mole of castor oil. By pouring the solution into water and uniformly distributing it therein, an aqueous dispersion is obtained. III. 20 parts by weight of compound no. 94 is dissolved in a mixture consisting of 40 Parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 116 is dissolved in a mixture consisting of 25 parts by weight of cyclohexanol, 65 Parts by weight of a mineral oil fraction-having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained. V. 80 parts by weight of compound no. 74 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained. VI. 3 parts by weight of compound no. 89 is intimately mixed with 97 Parts by weight of particulate kaolin. A dust is obtained containing 3% by weight of the active ingredient. VII. 30 parts by weight of compound no. 94 is intimately mixed with a mixture consisting of 92 parts by weight of powdered silica gel and 8 parts by weight of paraffin oil which has been sprayed onto the surface of this silica gel. A formulation of the active ingredient is obtained having good adherence. VIII. 40 parts by weight of compound no. 116 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion. IX. 20 parts by weight of compound no. 74 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained. In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum. The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebisthiocarbamyl disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
0,0-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenylsulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide,
3 2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-p-tert.-butylphenyl)-2-methylpropyl]-piperidine,
1-[2-(2,4-dichlorophenyl)-4-ethyl-1,3-dioxolan-2-ylethyl]-1H-1,2,4triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol, 1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methyl-pyrimidine,
bis-(p-chlorophenyl-3-pyridinemethanol,
1,2-bis-(3-ethoxycarbonyl-2-thioureido)-benzene,
1,2-bis-(3-methoxycarbonyl-2-thioureido)-benzene,
and various fungicides, such as
dodecylguanidine acetate,
3-[3-(3,5-dimethyl-2-oxycyclohexyl-2-hydroxyethyl)-glutaramide, hexachlorobenzene.
DL-methyl-N-(2,6-dimethylphenyl-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3.5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use Example

The compound 1-(1,2,4-triazol-1-yl)-2-(2-(2,4-dichlorophenyl)-pentane (A) disclosed in Thomson, Agricultural Chemicals, Book IV, Fungicides, page 124, 1988. was used for comparison purposes. Action on Botrytis cinerea in pimientos Pimiento seedlings of the "Neusiedler Ideal Elite" variety with 4 to 5 well developed leaves were sprayed to runoff with aqueous suspensions containing (dry basis) 80% of active ingredient and 20% of emulsifier. After the sprayed-on layer had dried, the plants were sprayed with a conidial suspension of the fungus Botrytis cinerea and kept in a highhumidity chamber at 22 to 24° C. After 5 days, the disease had spread on the untreated control plants to such an extent that the necroses covered the major portion of the leaves. The results show that active ingredients 74, 89, 94 and 116, applied as 0.05wt% spray liquors, have a better fungicidal action (97%) than prior art active ingredient A (60%).

We claim:

1. A process for preparing a 1-halo-1-azolylethane derivative of the formula

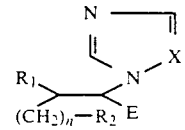

where
R$^1$ and R$^2$ are C$_1$-C$_8$-alkyl, phenyl, biphenyl, naphthyl, benzyl C$_3$-C$_8$-cycloalkyl or C$_3$-C$_8$-cycloalkenyl, each of which is unsubstituted or substituted by halogen, nitro, phenoxy, alkyl, alkoxy, amino or haloalkyl, each of 1 to 4 carbon atoms,
n is an integer from 1 to 5, or 0,
E is Cl or Br, and
X is CH or N,
wherein a compound of the formula:

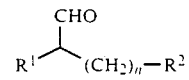

wherein R$^1$, R$^2$ and n have the above meanings, is reacted with a compound of the formula:

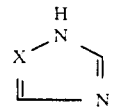

where X has the above meanings, in the presence of a thionyl halide of the formula SOE$_2$, where E is Cl or Br.

2. The process as set forth in claim 1, where R$^1$ is phenyl, R$^2$ is methyl, E is chlorine, X is N and n is 0.

3. The process as set forth in claim 1, where R$^1$ is 4-fluorophenyl, R$^2$ is 2-fluorophenyl, E is chlorine, X is CH and n is 0.

4. The process as set forth in claim 1, where R$^1$ is 2,4-dichlorophenyl, R$^2$ is methyl, E is chlorine, X is CH and n is 1.

5. The process as set forth in claim 1, where R$^1$ is 2,4-dichlorophenyl, R$^2$ is methyl, E is chlorine, X is CH and n is 3.

* * * * *

UNITED STATES PATENT AND TRADEMARK OFFICE
CERTIFICATE OF CORRECTION

PATENT NO. : 5,039,815
DATED : August 13, 1991
INVENTOR(S) : Rainer Seele et al.

It is certified that error appears in the above-identified patent and that said Letters Patent is hereby corrected as shown below:

On title page, item [54] and col. 1, lines 2-3, should be, --1-HALO-1-AZOLYLETHANE DERIVATIVES AND FUNGICIDES CONTAINING THEM--.

Signed and Sealed this

Ninth Day of March, 1993

*Attest:*

STEPHEN G. KUNIN

*Attesting Officer*   *Acting Commissioner of Patents and Trademarks*